(12) United States Patent
Shih et al.

(10) Patent No.: US 7,458,284 B2
(45) Date of Patent: Dec. 2, 2008

(54) THREE-STAGE DUST SAMPLER

(75) Inventors: Tung-Sheng Shih, Taipei Hsien (TW); Da-Toung Tang, Taipei (TW); Chuen-Jinn Tsai, Hsinchu (TW); Cheng-Sheng Chang, Hsinchu (TW)

(73) Assignee: Institute of Occupational Safety and Health, Council of Labor Affairs, Taipei Hsien (TW)

( * ) Notice: Subject to any disclaimer, the term of this patent is extended or adjusted under 35 U.S.C. 154(b) by 138 days.

(21) Appl. No.: 11/541,737

(22) Filed: Oct. 3, 2006

(65) Prior Publication Data

US 2007/0269349 A1 Nov. 22, 2007

(30) Foreign Application Priority Data

May 19, 2006 (TW) ............... 95208748 U

(51) Int. Cl.
*G01N 1/24* (2006.01)
(52) U.S. Cl. ............... 73/863.23; 73/863.21; 73/863.22
(58) Field of Classification Search . 73/863.21–863.25, 73/864.91
See application file for complete search history.

(56) References Cited

U.S. PATENT DOCUMENTS

| | | | | | |
|---|---|---|---|---|---|
| 4,387,603 | A | * | 6/1983 | Nelson | 73/863.22 |
| 4,640,140 | A | * | 2/1987 | Burghoffer et al. | 73/863.22 |
| 4,670,135 | A | * | 6/1987 | Marple et al. | 209/143 |
| 4,740,220 | A | * | 4/1988 | Mark et al. | 73/863.22 |
| 4,796,475 | A | * | 1/1989 | Marple | 73/863.22 |
| 4,820,925 | A | * | 4/1989 | Balmer et al. | 250/379 |
| 4,961,916 | A | * | 10/1990 | Lesage et al. | 422/88 |
| 4,972,957 | A | * | 11/1990 | Liu et al. | 209/143 |
| 5,343,767 | A | * | 9/1994 | Marple et al. | 73/863.22 |
| 6,101,886 | A | * | 8/2000 | Brenizer et al. | 73/863.23 |
| 6,226,852 | B1 | * | 5/2001 | Gundel et al. | 29/458 |

(Continued)

FOREIGN PATENT DOCUMENTS

DE 3543489 A1 * 6/1987

(Continued)

OTHER PUBLICATIONS

Koch et al., "Evaluation of the Respicon as a personal inhalable sampler in industrial environments", Aug. 28, 2002.*

(Continued)

*Primary Examiner*—David A. Rogers
(74) *Attorney, Agent, or Firm*—Bacon & Thomas PLLC

(57) ABSTRACT

A three-stage dust sampler makes use of a porous foam as the impactor substrates. The sampler includes an annular inlet which conforms to ISO/CEN/ACGIH inhalable sampling criteria, two impactor stages to classify thoracic and respirable particles and a final filter to collect respirable particles after the impactors. For 100 ppi polymer foam substrates, and a flow rate of 3.2 lpm, the collection efficiency curves of the thoracic and respirable dust matches ISO/CEN/ACGIH criteria when the jet-to-plate distance is 1.0. The cut-off aerodynamic diameter is 9.6 and 4.0 μm for the first and second impactor stages, respectively, and $\sqrt{stk_{50}}$ is 0.39 for both stages. The collection efficiencies for solid particles is equal to that for liquid particles, indicating that there is no solid particle bouncing from the foam substrates.

12 Claims, 6 Drawing Sheets

U.S. PATENT DOCUMENTS

| | | | |
|---|---|---|---|
| 6,240,768 B1 * | 6/2001 | Lemonnier | 73/28.05 |
| 6,431,014 B1 * | 8/2002 | Liu et al. | 73/863.22 |
| 6,786,105 B1 * | 9/2004 | Sioutas | 73/863.22 |
| 7,082,811 B2 * | 8/2006 | Marple et al. | 73/28.05 |
| 7,140,266 B2 * | 11/2006 | Marjamaki et al. | 73/865.5 |
| 7,232,477 B2 * | 6/2007 | Rodgers | 96/413 |
| 2001/0045000 A1 * | 11/2001 | Gundel et al. | 29/458 |
| 2005/0028616 A1 * | 2/2005 | Marple et al. | 73/863.22 |

FOREIGN PATENT DOCUMENTS

| | | |
|---|---|---|
| EP | 352126 A2 * | 1/1990 |
| GB | 2071518 A * | 9/1981 |

OTHER PUBLICATIONS

"Respicon Particle Sampler Brochure", TSI Incorporated, Jan. 1999.*

* cited by examiner

THREE-STAGE DUST SAMPLER

BACKGROUND OF THE INVENTION

1. Field of the Invention

The present invention relates to a three-stage dust sampler, and more particularly, to a dust sampler for collecting IPM (inhalable particulate mass), TPM (thoracic particulate mass), and RPM (respirable particulate mass) dust samples.

2. Description of the Related Art

ISO, CEN and ACGIH have proposed three sampling efficiency criteria as new international standards, which classify dust entering the head airways as IPM (inhalable particulate mass), dust entering the bronchia as TPM (thoracic particulate mass), and dust entering the gas exchange region as RPM (respirable particulate mass). ACGIH is an acronym for the American Conference of Governmental Industrial Hygienists, ISO is an acronym for the International Standards Organization, and CEN is an acronym for the Comite Europeen de Normalisation.

Most samplers can only sample one type of dust; for example, the IOM sampler (IOM personal inhalable sampler, SKC Inc.) can only sample IPM; 10 mm nylon cyclone and the IOSH cyclone developed by the applicants can only sample RPM. The Model 8522 Respicon sampler from TSI (Thermo System Incorporated, St. Paul) is the only sampler that can sample the above three different dust types at the same time; this sampler meets the sampling efficiency criteria of ISO/CEN/ACGIH, but is large in size, is expensive, and these flow rates is not easy to be calibrated.

The Respicon makes use of three virtual impactors to sample the three kinds of dust, IPM, TPM and RPM simultaneously (Model 8522 operation and service manual). Previous researches show that when the Respicon sampler is used for sampling dust concentrations, the results are not identical to those of the TSI. The concentration of each kind of dust is lower than the true value.

Therefore, it is desirable to provide a dust sampler for collecting IPM (inhalable particulate mass), TPM (thoracic particulate mass), and RPM (respirable particulate mass) simultaneously using only one flow rate to operate and different operation principles.

SUMMARY OF THE INVENTION

To solve the above-mentioned problem, a primary objective of the present invention is to provide a new three-stage dust sampler, which meets the international standards for the three dust types (IPM, TPM and RPM) and which furthermore is easy to operate, inexpensive, and has only one flow rate to operate.

A three-stage dust sampler constructed according to the present invention comprises:

a cap;

an inlet element having a hollow column, the hollow column having a radial baffler inside and an inlet nozzle at the center of the baffler;

a base having a hollow column, the hollow column having a bottom plate, a top opening and an outlet adapted to be connected to a pump, the outlet passing through the hollow column;

two-stage impactors connecting the inlet element to the base, the two-stage impactors comprising:

a first foam substrate supporting element having a hollow column, the hollow column having a radial baffler and 6 nozzles passing through the baffler and annularly surrounding the center of the baffler;

a second foam substrate supporting element having a hollow column, the hollow column having a radial baffler and 6 nozzles passing through the baffler and annularly surrounding the center of the baffler;

a third foam substrate supporting element having a hollow column, a dish and a plurality of radial arms holding the dish in the hollow column and at the center of the hollow column to form a plurality of channels between the hollow column and the dish;

a first foam substrate mounted on the radial baffler of the first foam substrate supporting element with the nozzles passing through the baffler of the first foam substrate supporting element being exposed and surrounded by the first foam substrate;

a second foam substrate mounted on the radial baffler of the second foam substrate supporting element and adjacent to the nozzles passing through the baffler of the second foam substrate supporting element;

a third foam substrate mounted on the dish of the third foam substrate supporting element; and a final filter, wherein the inlet element, the first foam substrate supporting element, the second foam substrate supporting element and the third foam substrate supporting element are all hermetically cascaded one by one;

the cap is fixed on the inlet element with an interval therebetween so that an annular inlet surrounding the inlet nozzle is formed between the cap and the inlet element;

one free end of the third foam substrate supporting element is hermetically connected to the top opening of the base, and the final filter clamped between the third foam substrate supporting element and the base; and when the outlet of the base is connected to a pump, an air flow enters the inlet nozzle of the inlet element via the annular inlet, contacts the first foam substrate, passes through the nozzles of the first foam substrate supporting element, contacts the second foam substrate, passes through the nozzles of the second foam substrate supporting element, contacts the third foam substrate, passes through the channels of the third foam substrate supporting element, passes through the final filter, and enters the outlet of the base to exit from the dust sampler.

Preferably, the first foam substrate, the second foam substrate and the third foam substrate are made of identical or different porous foams. More preferably, the first foam substrate, the second foam substrate and the third foam substrate are made of polyurethane (PU) foam. The PU foam preferably has 50-200-ppi (pores-per-inch), and more preferably 100 ppi.

Preferably, the cap has a diameter of 51 mm, and the interval between the cap and the inlet element is 3.0 mm. More preferably, the inlet nozzle of the inlet element has a diameter of 18 mm.

Preferably, the radial baffler of the first foam substrate supporting element has a diameter of 47 mm and six upright nozzles, wherein each of the upright nozzles has a diameter of 3.5 mm, and the first foam substrate has an outer diameter 47 mm and six through holes corresponding to the six upright nozzles, wherein the six upright nozzles are received in the six through holes of the first foam substrate.

Preferably, the radial baffler of the second foam substrate supporting element has a diameter of 47 mm, six nozzles, and a raised portion with a diameter of 15 mm at the center of the radial baffler, wherein the six nozzles are disposed on the raised portion and close to a periphery of the raised portion, and each nozzle has a diameter of 2.0 mm, and wherein the second foam substrate is a ring with an outer diameter of 47 mm and an inner diameter of 15 mm, and the ring surrounds the raised portion.

Preferably, wherein the hollow column of the third foam substrate supporting element has an inner diameter of 47 mm, and the third foam substrate is circular and has an outer diameter 22 mm.

Preferably, the first foam substrate, the second foam substrate and the third foam substrate all have thicknesses of about 4-10 mm, and more preferably 6 mm.

The sampler of the present invention differs from the Respicon sampler, which uses two virtual impactors. The sampler uses an annular inlet to sample IPM and the following two-stage impactors using porous foams as the collection substrates to sample TPM and RPM, respectively. In the impactors, some air flow penetrate into the foam substrate, creating smoother collection efficiency curves which can be matched with the criteria sampling efficiency of TPM and RPM. The traditional impactor uses a flat plate as collection substrate will have a very sharp collection efficiency curve too sharp to match with ISO/CEN/ACGIH criteria curves. The porous foam has another advantage. It can prevent solid particle bounce back from the substrate.

Other objects, advantages, and novel features of the invention will become more apparent from the following detailed description when taken in conjunction with the accompanying drawings.

DETAILED DESCRIPTION OF THE PREFERRED EMBODIMENT

Figure 1:
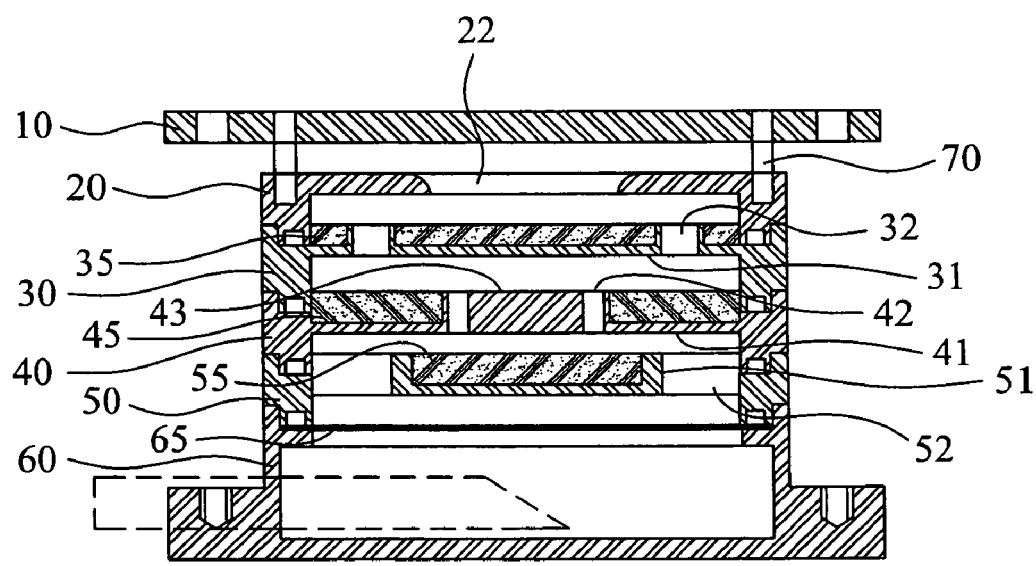
FIG. 1 is a schematic cross-sectional view showing a dust sampler constructed according to one of the preferred embodiments of the present invention.
Figure 2:
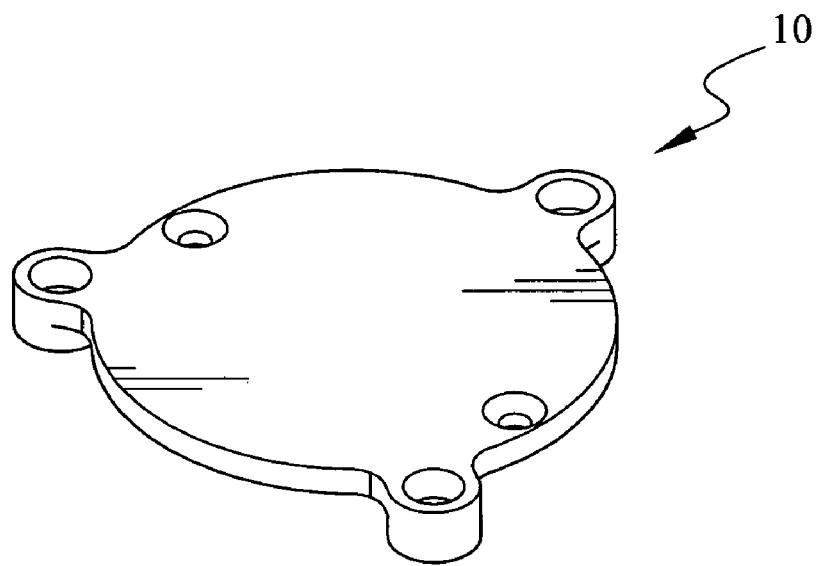
FIG. 2 shows the cap 10 depicted in FIG. 1.
Figure 3:
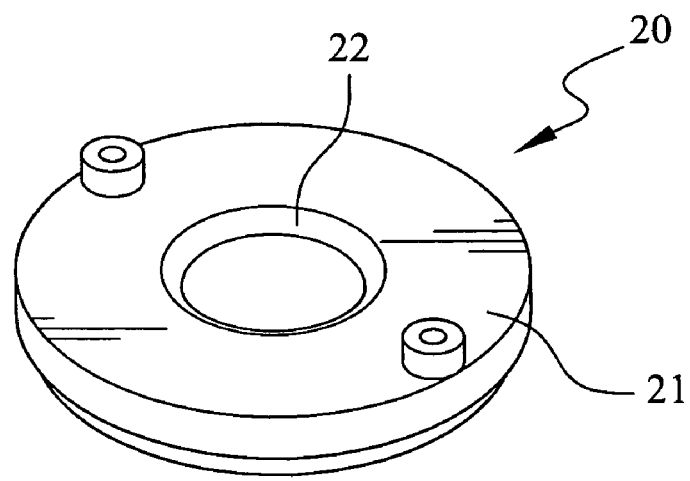
FIG. 3 is a schematic perspective view of the inlet element 20 shown in FIG. 1.
Figure 4:
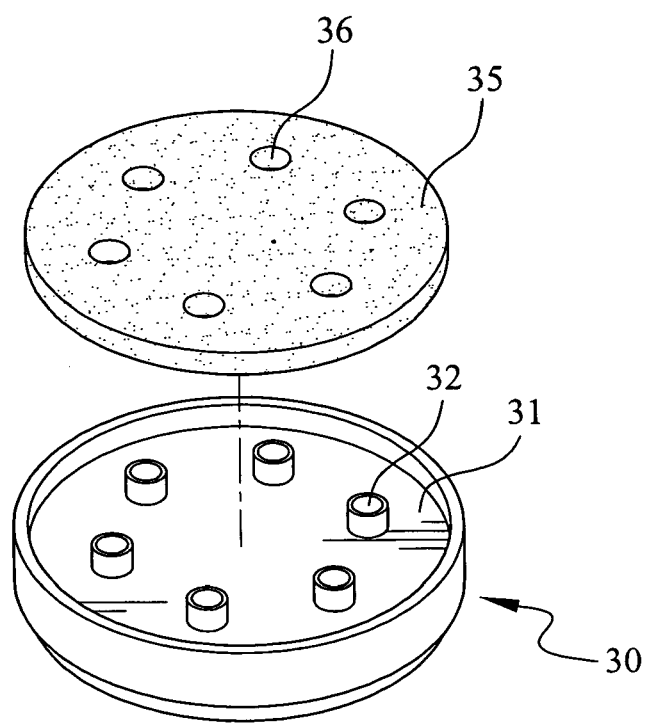
FIG. 4 is a schematic perspective view showing the first foam substrate 35 and its supporting element 30 depicted in FIG. 1.
Figure 5:
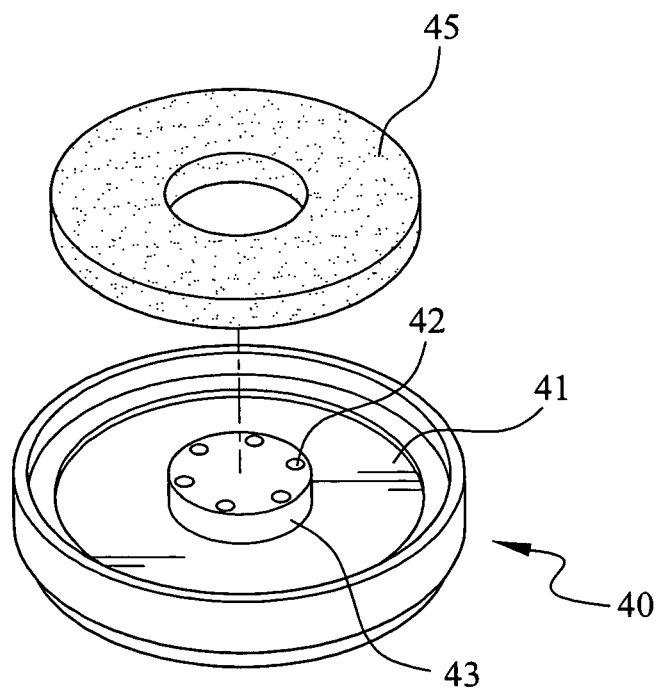
FIG. 5 is a schematic perspective view showing the second foam substrate 45 and is supporting element 40 depicted in FIG. 1.
Figure 6:
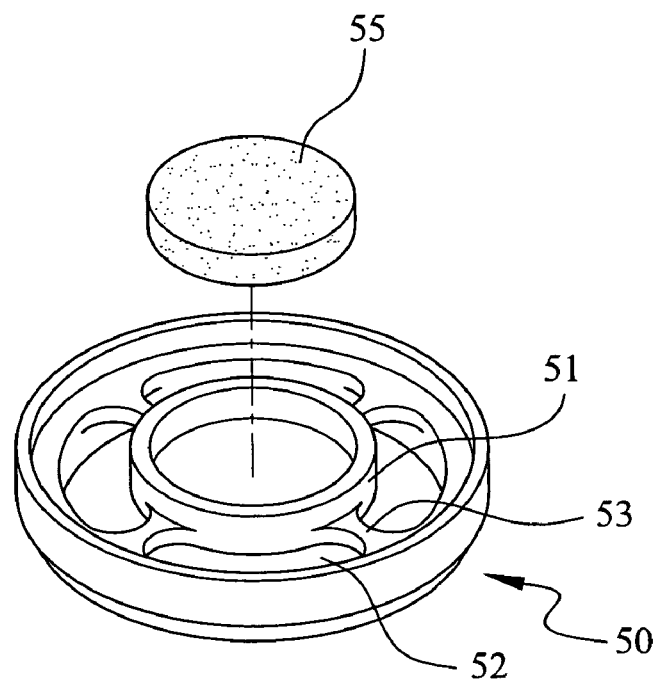
FIG. 6 is a schematic perspective view of the third foam substrate 55 and its supporting element 50 depicted in FIG. 1
Figure 7:
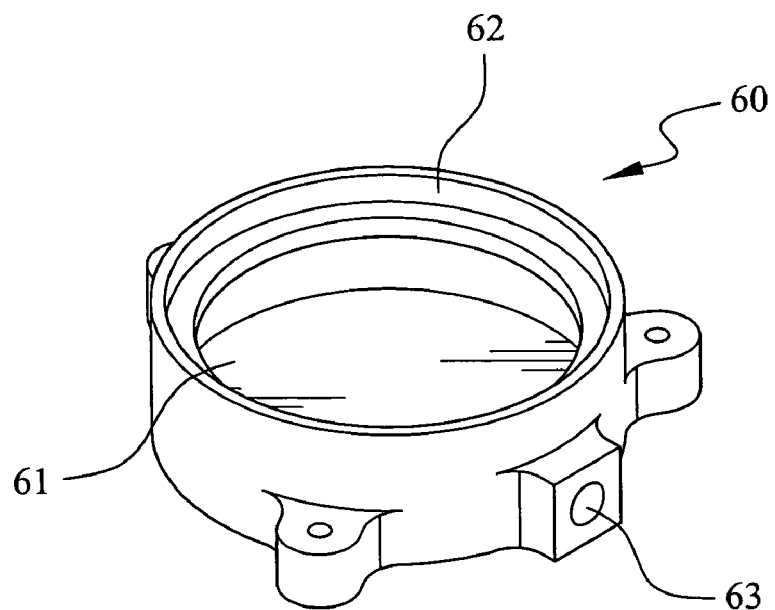
FIG. 7 is a schematic perspective view of the base 60 depicted in FIG. 1.

A three-stage dust sampler constructed according to one of the preferred embodiments of the present invention, which is able to collect IPM (inhalable particulate mass), TPM (thoracic particulate mass) and RPM (respirable particulate mass) data, is shown in FIG. 1 to FIG. 7. The dust sampler comprises an inlet element 20, a cap 10 connected to the inlet element 20, a base 60 and two-stage impactors (30,40,50) for connecting the inlet element 20 to the base 60. The base 60 is a hollow columnar body and has a bottom plate 61, a top opening 62 and an outlet 63 passing though the hollow columnar body of the base 60 for connecting to a pump. The cap 10 and the inlet element 20 form an annular inlet through which the dust particles enter the sampler circumferentially (FIGS. 1, 2 and 3). The inlet element 20 has a radial baffle 21 forming an inlet nozzle 22 at the center of the baffle 21, as shown in FIG. 3. The particles then enter the inlet nozzle 22 disposed at the center of the inlet element 20 (FIG. 3) and are collected on the porous foam substrates 35, 45 and 55 in FIGS. 4, 5, and 6 and the after filter 65 in FIG. 7. By properly design the gap between the cap 10 and the inlet element 20, and the diameter of the cap 10, particles collected after the nozzle 22 are called IPM. That is, IPM is the sum of the particles masses collected on the porous foams 35(FIG. 4), 45 (FIG. 5), 55 (FIG. 6), and the after filter 65 (FIG. 7). The first stage impactor includes a first foam substrate supporting element 30 having a hollow column, and the hollow column thereof having a radial baffler 31 and six vertical nozzles 32 passing through the baffler 31 and annularly surrounding the center of the baffler 31 (FIG. 4); a second foam substrate supporting element 40 having a hollow column, and the hollow column thereof having a radial baffler 41. The second stage impactor includes six nozzles 42 and a raised portion 43 at the center of the radial baffler 41, wherein the six nozzles 42 are formed on the raised portion 43 separately and close to a periphery of the raised portion 43 (FIG. 5); a third foam substrate supporting element 50 having a hollow column, a dish 51 and four radial arms 53 holding the dish 51 at the inner center of the hollow column to form four channels 52 between the dish 51 and the hollow column of the supporting element 50 (FIG. 6). The two-stage impactors further include a first foam substrate 35 having six through holes 36 corresponding to the six vertical nozzles 32, wherein the six through holes 36 of the first foam substrate receive the six vertical nozzles 32 to mount the first foam substrate 35 on the radial baffler 31 of the first foam substrate supporting element 30 (FIG. 4); a second foam substrate 45 having an annular shape and mounted on the raised portion 43 of the second foam substrate supporting element 40 (FIG. 5); a third foam substrate 55 having a round shape and mounted in the dish 51 of the third foam supporting element 50 (FIG. 6).

The inlet element 20, the first foam substrate supporting element 30, the second foam substrate supporting element 40 and the third foam substrate supporting element 50 are all hermetically cascaded one by one. The cap 10 is fixed on the inlet element 20 by two bolts 70 with a gap therebetween, so that an annular inlet surrounding the inlet nozzle 22 is formed between the cap 10 and the inlet element 20. The free end of the third foam substrate supporting element 50 is hermetically connected to the top opening 62 of the base 60, and the final filter 65 is clamped between the third foam substrate supporting element 50 and the base 60.

When the outlet 63 of the base 60 is connected to a pump, an air stream will enter the annular inlet where particles larger than IPM will be collected. IPM particles will enter the inlet nozzle 22 of the inlet element. Particles larger than 30 μm in aerodynamic diameter will be impacted on the first foam substrate 35, smaller particles and air stream will continue passing through the nozzle 32 of the first foam substrate supporting element 30, particles greater than 10 μm in aerodynamic diameter will impact on the second foam substrate 45, particles less than 10 μm and the air stream will pass the nozzle 42 of the second foam substrate supporting element 40, particles less than 4 μm in aerodynamic diameter will impact on the third foam substrate 55, particles less than 4 μm and air stream will through the channels 52 in the third foam substrate supporting element 50, all particles will be collected by the final filter 65, and the air stream will enter the outlet 63 of the base 60 to exit from the dust sampler.

The cap 10 has a diameter of 51 mm. The gap between the cap 10 and the inlet element 20 is 3.0 mm.

The inlet nozzle 22 of the inlet element has a diameter of 18 mm.

The radial baffler 31 of the first foam substrate supporting element 30 has a diameter of 47 mm, and the six nozzles 32 all have a diameter of 3.5 mm.

The radial baffler 41 of the second foam substrate supporting element has a diameter of 47 mm, the raised portion 43 has a diameter of 15 mm, and the nozzles 42 all have a diameter of 2.0 mm.

The hollow column of the third foam substrate supporting element 50 has an inner diameter 47 mm, and the dish 51 has an inner diameter of 22 mm.

The sampler of the present invention shown in FIG. 1 to FIG. 7 can collect three different types of dust (IPM, TPM and RPM), and is formed by the inhalable annular inlet, the first and the second stage impactors and the final filter. The inhalable annular inlet is formed by the cap 10 and the inlet element 20 and is for catching particles larger than IPM. IPM is collected after the inlet nozzle of the inlet element 20. The first stage impactor is a TPM impactor of 10 µm cutoff diameter, which is formed by the six nozzles 32 on the first foam substrate supporting element 30 and the second foam 45 on the second foam substrate supporting element 40, and is used for catching particles larger than TPM. The second stage impactor is a RPM impactor formed by the six nozzles 42 on second foam substrate supporting element 40 and the third foam 55 on the third foam substrate supporting element 50, and is for catching particles larger than RPM. The final filter 65 is provided to collect RPM dust. The sum of the particle mass on the third foam 55 and RPM is called TPM. The sum of the particle mass on the first foam 35, second foam 45 and TPM is called IPM.

The first stage and second stage impactors are designed with a $\sqrt{stk_{50}}=0.39$ according to the trial-and-error method, at a flow rate of 3.2 lpm (liter/min). There are six impactor nozzles at the first stage, with the nozzle diameter of 3.5 mm. At the same flow rate, the second stage impactor has six round nozzles with the nozzle diameter of 2.0 mm. The impactors uses a porous foams as the collection substrate to make the particle collection efficiency curves smooth. That is the present invention uses a porous substrate to replace the conventional plate-like collection substrate, which has a collect efficiency curve too sharp to meet with the ISO/CEN/ACGIH criteria curves. The first foam substrate 35, the second foam substrate 45 and the third foam substrate 55 are made of polyurethane (PU) foam (Foamex Inc., Pennsylvania, USA), and the PU foam substrates have 100 ppi (pores-per-inch) and a thickness of 6 mm. The outer diameter of the first foam substrate 35 is 47 mm, and the six through holes 36 all have a diameter of 3.5 mm. The second foam substrate 45 has an outer diameter of 47 mm and an inner diameter of 15 mm. The outer diameter of the third foam substrate 55 is 22 mm.

A laboratory test was performed to determine the collection efficiency curves, which utilized liquid particles (oleic acid) and solid particles (a standard PSL fluorescent particle). The 2-20 µm single-diameter liquid particles were generated by a vibrating orifice monodisperse aerosol generator (VOMAG, TSI Model 3450, TSI INC. St. Paul, Minn.), dried and neutralized by a Kr-85 Neutralizer, and were used to test the impactors. The diameter of the monodisperse particles was verified by an aerodynamic particle sizer (APS, TSI Model 3321). The foam substrates, the final filter and the internal wall of the sampler were separately extracted with an aqueous solution of 0.001 N NaOH. A fluorometer (Turner 10-AU, Cincinnati U.S.A.) was used for measuring the collection efficiency and the internal loss rate of the dust sampler.

In order to determine whether the solid particle collection efficiency is similar to the liquid particle collection efficiency when PU foam substrates are used as collection panels, monodisperse solid fluorescent PSL particles were also used to test the sampler. A TSI small scale powder disperser (Model 3433, TSI Inc., St Paul, Minn., USA) was used to introduce the monodisperse solid PSL fluorescent particles (Duke Scientific, Palo Alto, Calif.) into a test chamber for testing the sampler. The fluorescent particles collected by the PU foam substrates and the final filter were extracted with xylene, and a fluorometer was used to measure the fluorescence, thereby the particle collection efficiency and particle loss of the dust sampler can be calculated.

The Results

Figure 8:
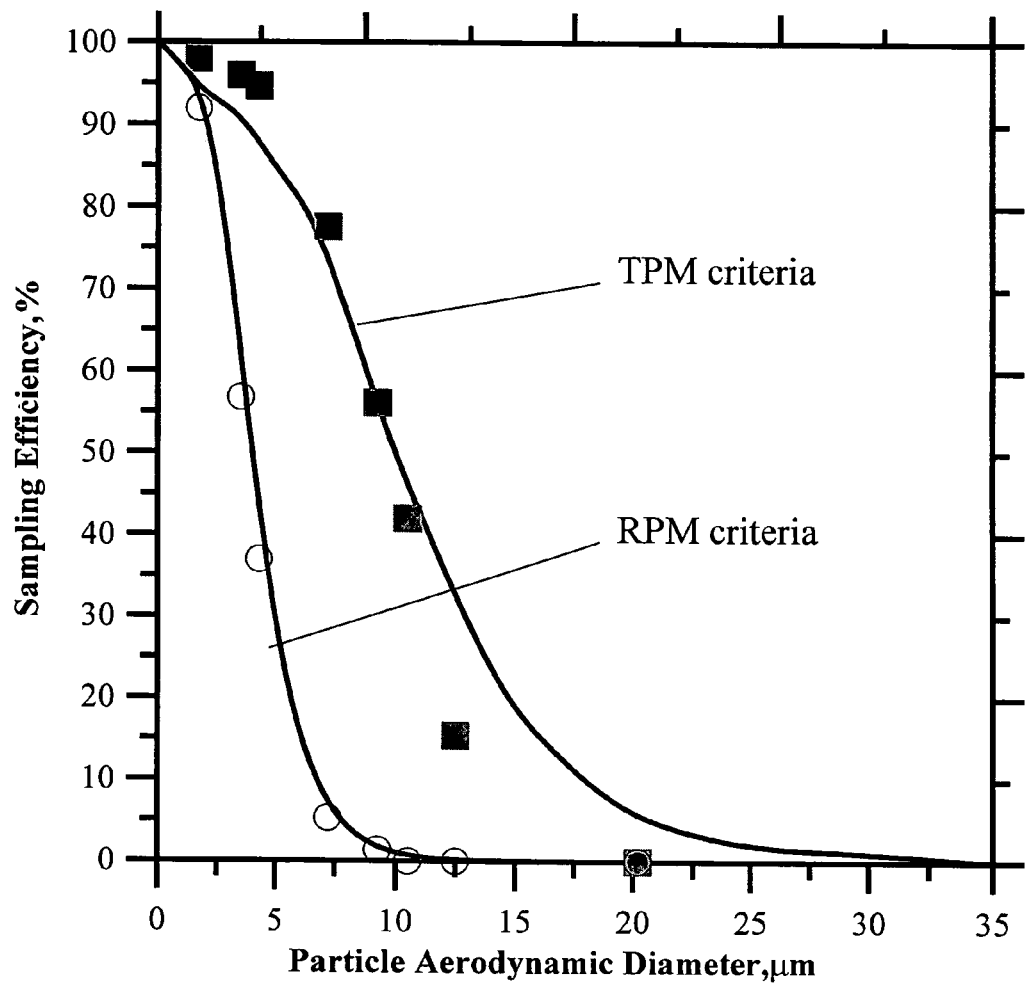
FIG. 8 is a sampling efficiency (%) vs. particle aerodynamic diameter plot for liquid particles collected with the dust sampler shown in FIG. 1.
Figure 9:
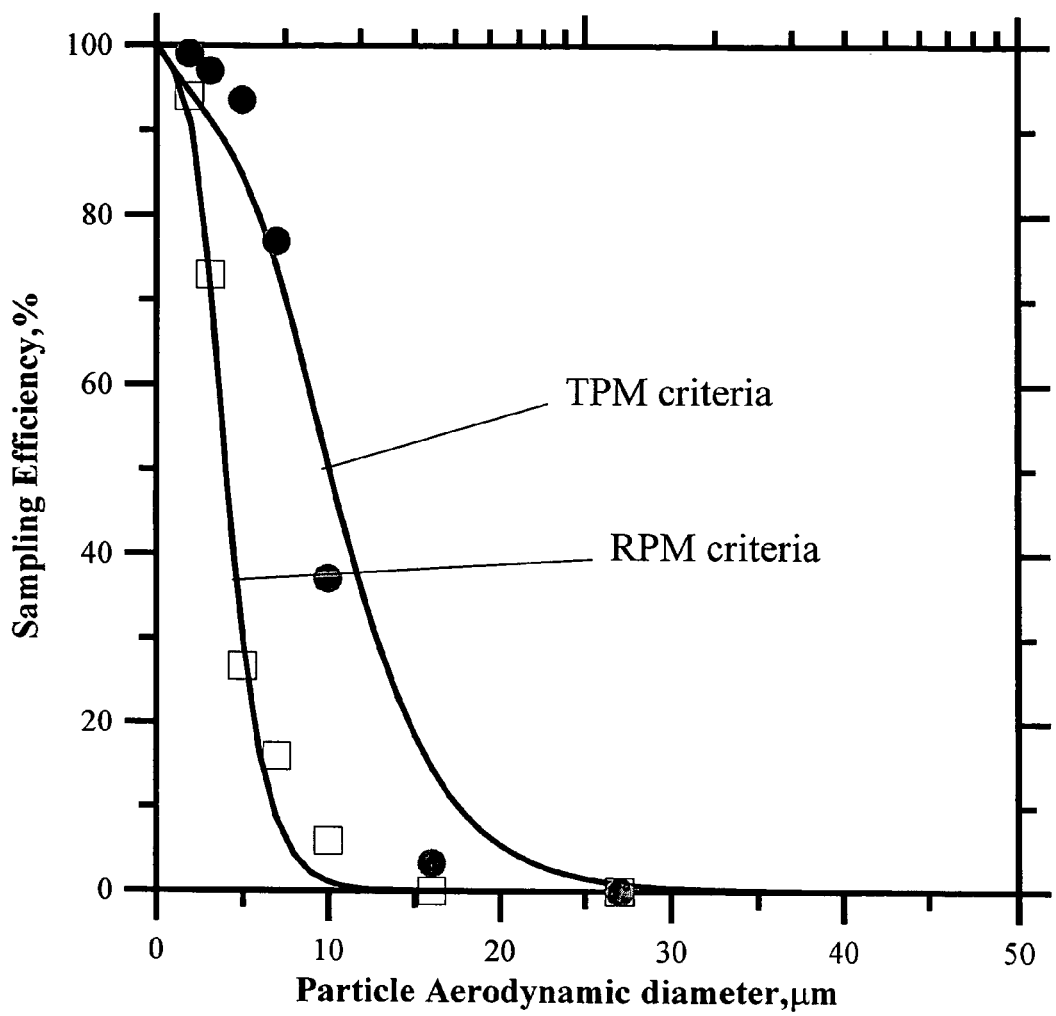
FIG. 9 is a sampling efficiency (%) vs. particle aerodynamic diameter plot for solid particles collected with the dust sampler shown in FIG. 1.

FIG. 8 shows the liquid particle collection efficiency curve of the dust sampler of the present invention. FIG. 9 shows a solid particle collection efficiency curve of the dust sampler of the present invention. It can be seen from FIG. 8 and FIG. 9, where PU foam substrates were used as the impact substrates, the particle collection efficiency curves match with the TPM and RPM of the ISO/CEN/ACGIH standards, and the errors of the collection efficiency curves are within positive and negative 12%. It was also found that the internal wall particle loss of this dust sampler at each impact stage is all close to zero. It can be seen from FIG. 8 and FIG. 9, the RPM cut-off aerodynamic diameter is very close to 4 µm which is set by the ISO/CEN/ACGIH standards; the TPM cut-off aerodynamic diameter is 9.6 µm, which only has a 4% error in comparison with the cut-off aerodynamic diameter of 10 µm set by the ISO/CEN/ACGIH standards. The solid particle penetration efficiency curve shown in FIG. 9 is almost identical to the liquid particle penetration efficiency curve shown in FIG. 8. This indicates that the PU foam substrates have the ability to prevent solid particles from bouncing from the PU foam substrates. In view of the above, when a PU foam substrate with 100 ppi is used as the collection plate, and the sampling is at the flow rate of 3.2 lpm, the particle penetration efficiency curve of the dust sampler of the present invention matches the ISO/CEN/ACGIH sampling efficiency criteria.

The inventors of the present application have used the dust sampler of the present invention, the Marple personal sampler, the IOSH cyclone, and the Respicon sampler in three different working environments to perform comparison tests on the IPM, TPM and RPM concentrations. The comparison results show that the dust sampler of the present invention has an accuracy that is better than the Respicon sampler in sampling the three types of dust.

Although the present invention has been explained in relation to its preferred embodiment, it is to be understood that many other possible modifications and variations can be made without departing from the spirit and scope of the invention as hereinafter claimed.

What is claimed is:

1. A three-stage dust sampler comprising:
   a cap;
   an inlet element having a hollow column, the hollow column having a radial baffler inside and an inlet nozzle at the center of the baffler;
   a base having a hollow column, the hollow column having a bottom plate, a top opening and an outlet adapted to be connected to a pump, the outlet passing through the hollow column;
   two-stage impactors connecting the inlet element to the base, the two-stage impactors comprising:

a first foam substrate supporting element having a hollow column, the hollow column having a radial baffler and 6 nozzles passing through the baffler and annularly surrounding the center of the baffler;

a second foam substrate supporting element having a hollow column, the hollow column having a radial baffler and 6 nozzles passing through the baffler and annularly surrounding the center of the baffler;

a third foam substrate supporting element having a hollow column, a dish and a plurality of radial arms holding the dish in the hollow column and at the center of the hollow column to form a plurality of channels between the hollow column and the dish;

a first foam substrate mounted on the radial baffler of the first foam substrate supporting element with the nozzles passing through the baffler of the first foam substrate supporting element being exposed and surrounded by the first foam substrate;

a second foam substrate mounted on the radial baffler of the second foam substrate supporting element and adjacent to the nozzles passing through the baffler of the second foam substrate supporting element;

a third foam substrate mounted on the dish of the third foam substrate supporting element; and a final filter, wherein the inlet element, the first foam substrate supporting element, the second foam substrate supporting element and the third foam substrate supporting element are all hermetically cascaded one by one;

the cap is fixed on the inlet element with an interval therebetween so that an annular inlet surrounding the inlet nozzle is formed between the cap and the inlet element;

one free end of the third foam substrate supporting element is hermetically connected to the top opening of the base, and the final filter clamped between the third foam substrate supporting element and the base; and when the outlet of the base is connected to a pump, an air flow enters the inlet nozzle of the inlet element via the annular inlet, contacts the first foam substrate, passes through the nozzles of the first foam substrate supporting element, contacts the second foam substrate, passes through the nozzles of the second foam substrate supporting element, contacts the third foam substrate, passes through the channels of the third foam substrate supporting element, passes through the final filter, and enters the outlet of the base to exit from the dust sampler.

2. The dust sampler as claimed in claim 1, wherein the first foam substrate, the second foam substrate and the third foam substrate are made of identical or different porous foams.

3. The dust sampler as claimed in claim 2, wherein the first foam substrate, the second foam substrate and the third foam substrate are made of polyurethane (PU) foam.

4. The dust sampler as claimed in claim 3, wherein the PU foam has 50-200 ppi (pores-per-inch).

5. The dust sampler as claimed in claim 4, wherein the PU foam have 100 ppi (pores-per-inch).

6. The dust sampler as claimed in claim 5, wherein the first foam substrate, the second foam substrate and the third foam substrate all have thicknesses of about 4-10 mm.

7. The dust sampler as claimed in claim 1, wherein the cap has a diameter of 51 mm, and the interval between the cap and the inlet element is 3.0 mm.

8. The dust sampler as claimed in claim 7, wherein the inlet nozzle of the inlet element has a diameter of 18 mm.

9. The dust sampler as claimed in claim 7, wherein the radial baffler of the first foam substrate supporting element has a diameter of 47 mm and six upright nozzles, wherein each of the upright nozzles has a diameter of 3.5 mm, and the first foam substrate has an outer diameter 47 mm and six through holes corresponding to the six upright nozzles, wherein the six upright nozzles are received in the six through holes of the first foam substrate.

10. The dust sampler as claimed in claim 9, wherein the radial baffler of the second foam substrate supporting element has a diameter of 47 mm, six nozzles, and a raised portion with a diameter of 15 mm at the center of the radial baffler, wherein the six nozzles are disposed on the raised portion and close to a periphery of the raised portion, and each nozzle has a diameter of 2.0 mm, and wherein the second foam substrate is a ring with an outer diameter of 47 mm and an inner diameter of 15 mm, and the ring surrounds the raised portion.

11. The dust sampler as claimed in claim 10, wherein the hollow column of the third foam substrate supporting element has an inner diameter of 47 mm, and the third foam substrate is circular and has an outer diameter 22 mm.

12. The dust sampler as claimed in claim 11, wherein the first foam substrate, the second foam substrate and the third foam substrate all have 6 mm thicknesses.

\* \* \* \* \*